(12) United States Patent
Krensky et al.

(10) Patent No.: US 10,039,867 B2
(45) Date of Patent: *Aug. 7, 2018

(54) INTRA-OPERATIVE BLOOD RECOVERY SYSTEM

(71) Applicant: PROCELL SURGICAL INC., Toronto (CA)

(72) Inventors: Robert Krensky, Toronto (CA); David G. Matsuura, Toronto (CA); Philip J. Simpson, Toronto (CA)

(73) Assignee: PROCELL SURGICAL INC., Toronto, Ontario (CA)

( * ) Notice: Subject to any disclaimer, the term of this patent is extended or adjusted under 35 U.S.C. 154(b) by 344 days.

This patent is subject to a terminal disclaimer.

(21) Appl. No.: 14/921,607

(22) Filed: Oct. 23, 2015

(65) Prior Publication Data

US 2016/0038656 A1  Feb. 11, 2016

Related U.S. Application Data

(63) Continuation of application No. 13/217,116, filed on Aug. 24, 2011, now Pat. No. 9,199,009.

(60) Provisional application No. 61/426,965, filed on Dec. 23, 2010, provisional application No. 61/444,501, filed on Feb. 18, 2011, provisional application No. 61/448,963, filed on Mar. 3, 2011.

(51) Int. Cl.
*A61M 1/00* (2006.01)
*A61M 1/02* (2006.01)
*A61M 1/36* (2006.01)

(52) U.S. Cl.
CPC ........ *A61M 1/0001* (2013.01); *A61M 1/0009* (2013.01); *A61M 1/0281* (2013.01); *A61M 1/3627* (2013.01); *Y10T 137/8593* (2015.04)

(58) Field of Classification Search
CPC ............ A61M 1/0001–1/0017; A61M 1/0056; A61M 1/024–1/0245; A61M 1/0259–1/0268; A61M 1/0272–1/0277
See application file for complete search history.

(56) References Cited

U.S. PATENT DOCUMENTS

| | | | |
|---|---|---|---|
| 9,199,009 B2 * | 12/2015 | Krensky | A61M 1/0001 |
| 2006/0057027 A1 * | 3/2006 | Hudak | A61B 10/0051 422/549 |
| 2007/0137504 A1 | 6/2007 | Wan et al. | |
| 2007/0282309 A1 | 12/2007 | Bengtson et al. | |
| 2009/0005747 A1 * | 1/2009 | Michaels | A61M 1/0001 604/319 |

FOREIGN PATENT DOCUMENTS

| | | |
|---|---|---|
| JP | S5626598 U | 3/1981 |
| JP | H05 277176 A | 10/1993 |
| JP | 2008296140 A | 12/2008 |

OTHER PUBLICATIONS

International Search Report for EP 11850638 dated Apr. 16, 2018, 4 Pages.

* cited by examiner

*Primary Examiner* — Benjamin Klein

(57) ABSTRACT

A method for recovering blood from a blood-laden surgical sponge for autologous reinfusion, the method comprising the steps of: conveying negative pressure to a housing with the blood-laden surgical sponge; applying a predetermined force to draw the blood from the surgical sponge; and collecting the recovered blood.

19 Claims, 8 Drawing Sheets

INTRA-OPERATIVE BLOOD RECOVERY SYSTEM

CROSS-REFERENCE TO RELATED APPLICATIONS

This application is a continuation of U.S. Non-Provisional application Ser. No. 13/217,116 filed on Aug. 24, 2011, which claims the benefit of priority to U.S. Provisional Application Ser. No. 61/426,965, filed on Dec. 23, 2010; U.S. Provisional Application Ser. No. 61/444,501, filed on Feb. 18, 2011; and U.S. Provisional Application Ser. No. 61/448,963 filed on Mar. 3, 2011.

FIELD OF THE INVENTION

The present invention relates to medical devices, and more particularly to intra-operative blood recovery systems.

BACKGROUND OF THE INVENTION

Autologous blood transfusion or autotransfusion is the collection and reinfusion of a patient's own blood products. Autologous blood is preferred in some instances because the blood type will always match, and if only autologous blood is used during surgery then the risk of exposure to infectious diseases, such as, hepatitis or HIV from blood, is substantially eliminated, and the risk of allergic reactions, or other adverse reactions, is significantly reduced.

Generally, during a surgical procedure autologous blood transfusion may be facilitated by either a blood processing device, such as a cell-saver type machine or a cardiopulmonary bypass (CPB) machine. The CPB machine is directly connected to the patient by tubing which allows for continuous recovery of blood from a body cavity and reinfusion of the patient's blood. The "cell-saver" method requires the recovered blood to be processed (spun, washed, etc.) and then bagged for reinfusion via a typical intravenous route.

Surgical sponges are also commonly used during surgical procedures to absorb body fluids of the patient, such as blood, both inside the incision or around the site of the surgery. Sponges of this nature are usually made of an open-meshed absorbent fabric, such as woven cotton. The sponge may be re-used or discarded and the process repeated as many times as is necessary during the surgical procedure. Typically, the blood is recovered from the sponge by either physically wringing the sponge or by soaking the sponge in a saline solution, and then the blood and saline solution are suctioned either into the cell saver where the red blood cells are washed, spun and returned to the patient, or directly by a CPB machine. The wringing method has a number of drawbacks, such as, loss of blood from splatter and residual blood remaining on hands. In addition, this method is time-consuming, inefficient, and has the potential to physically damage the blood cells due to the compressional and torsional forces. Furthermore, the amount of blood recovered from the sponges is variable, and depends on the individual's strength, technique and stamina. In addition, the wringing method is not particularly aesthetic and is generally considered as being undesirable by most users.

It is an object of an aspect of the following to mitigate or obviate at least one of the above-mentioned disadvantages.

SUMMARY OF THE INVENTION

In one aspect of the invention, there is provided an apparatus for recovering fluid from a fluid retaining structure, said apparatus comprising:

a vessel for receiving said fluid retaining structure, said vessel comprising a port; and wherein said port is coupled to a source of negative pressure, and said negative pressure is conveyed to said vessel to apply a force on said fluid retaining structure to cause egress of said fluid from said retaining structure.

In another of its aspects, there is provided a method for recovering fluid from a fluid retaining structure and collecting said fluid in a vessel, the method comprising the steps of:
  associating said vessel with a perforated barrier;
  introducing said fluid retaining structure to abut said barrier in said vessel;
  providing a force within said vessel to cause egress of said fluid from said fluid retaining structure; wherein
  said fluid passes through said perforated barrier into a reservoir of said vessel.

In another of its aspects, there is provided an apparatus for recovering blood from a sponge containing said blood, said apparatus comprising:
  a receptacle defining an internal chamber;
  a sponge retaining housing comprising a perforated base, said sponge retaining housing being received by said receptacle;
  at least one piston received by said sponge retaining housing, said at least one piston being caused to force said sponge against said perforated base; and
  wherein said blood is forced out of said sponge and said blood flows through said perforated base into said receptacle.

In another of its aspects, there is provided a method for monitoring blood loss, the method comprising the steps of:
  absorbing blood from a surgical site with a surgical sponge;
  removing said surgical sponge from said surgical site;
  introducing said sponge into a vessel, said vessel comprising at least one port;
  coupling said at least one port to a source of negative pressure outside said vessel; and
  operating said source of negative pressure to convey negative pressure to said vessel in response to said negative pressure forcing the egress of said fluid from said sponge;
  collecting said recovered blood received via said at least one aperture; and
  measuring the amount of recovered blood from said surgical sponge.

In another of its aspects, there is provided an apparatus for recovering blood from a sponge containing said blood, said apparatus comprising:
  a housing defining an internal cavity;
    said housing having an opening to introduce said sponge therein;
    a port to permit fluid flow from said internal cavity;
    a barrier intermediate said sponge and said port, said barrier having at least one aperture to allow fluid therethrough; and
  wherein said blood is forced out of said sponge by a force applied to said sponge.

In another of its aspects, there is provided a method for recovering blood from a blood-laden surgical sponge for autologous reinfusion, the method comprising the steps of:
  conveying negative pressure to a housing with said surgical sponge;
  applying a predetermined force to draw said blood from said surgical sponge; and
  collecting said recovered blood.

In another of its aspects, there is provided an apparatus for recovering blood from a sponge containing said blood, said apparatus comprising:
   a receptacle defining an internal chamber;
   a sponge retaining housing comprising a perforated base, said sponge retaining housing being received by said receptacle;
   a member received by said sponge retaining housing, said member caused to urge said sponge against said perforated base; and
   wherein said blood is forced out of said sponge and said blood flows through said perforated base into said receptacle.

Advantageously, the blood recovery apparatus is more effective in recovering blood from the blood-laden surgical sponges for autologous reinfusion than prior art methods. Furthermore, the apparatus is more consistent, potentially more effective, especially in long operating procedures, and potentially less damaging to the blood cells. Also, the apparatus allows for improved monitoring of blood loss from a patient.

BRIEF DESCRIPTION OF THE DRAWINGS

Several exemplary embodiments of the present invention will now be described, by way of example only, with reference to the appended drawings in which.

DETAILED DESCRIPTION OF EXEMPLARY EMBODIMENTS

Figure 1:
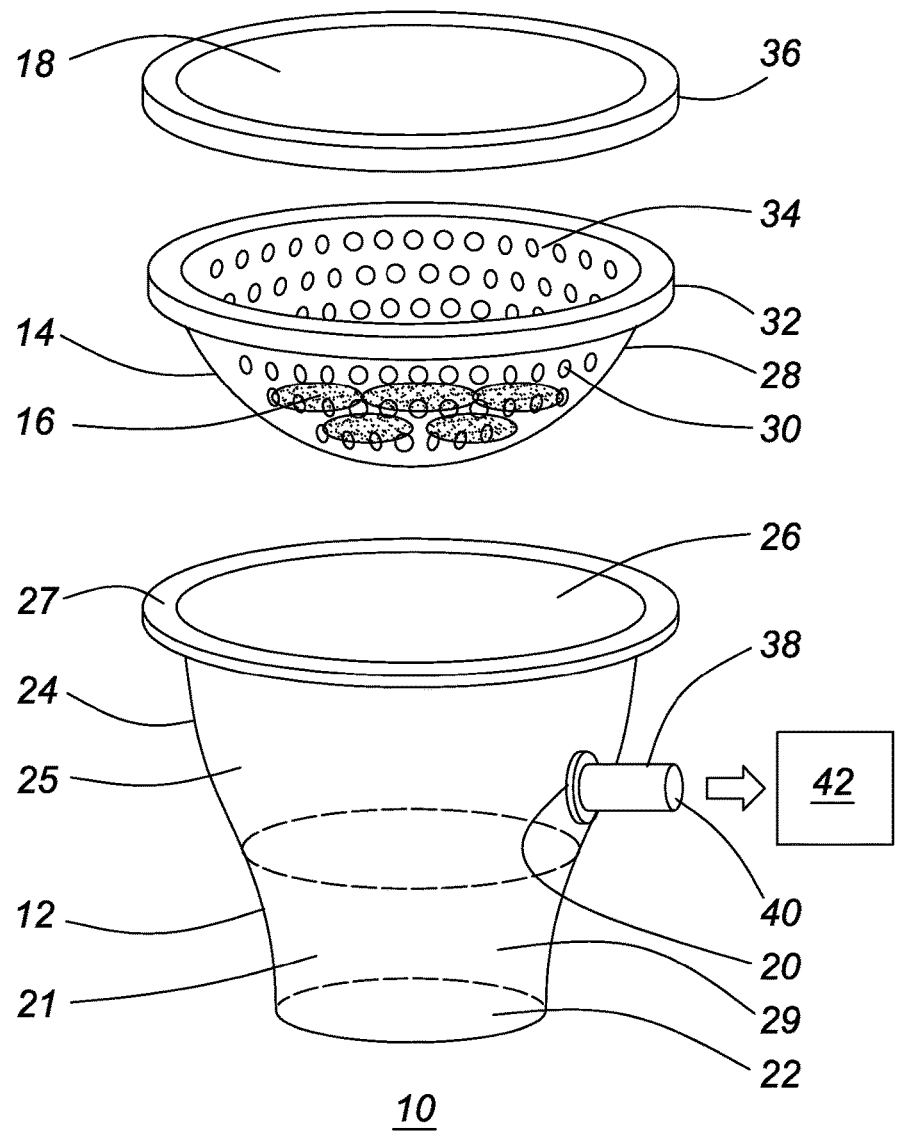
FIG. 1 shows an exemplary apparatus for recovering blood.

The detailed description of exemplary embodiments of the invention herein makes reference to the accompanying block diagrams and schematic diagrams, which show the exemplary embodiment by way of illustration and its best mode. While these exemplary embodiments are described in sufficient detail to enable those skilled in the art to practice the invention, it should be understood that other embodiments may be realized and that logical and mechanical changes may be made without departing from the spirit and scope of the invention. Thus, the detailed description herein is presented for purposes of illustration only and not of limitation. For example, the steps recited in any of the method or process descriptions may be executed in any order and are not limited to the order presented.

Moreover, it should be appreciated that the particular implementations shown and described herein are illustrative of the invention and its best mode and are not intended to otherwise limit the scope of the present invention in any way. Indeed, for the sake of brevity, certain sub-components of the individual operating components, and other functional aspects of the apparatus or systems may not be described in detail herein. Like elements in the various exemplary embodiments are represented by like reference numerals.

FIG. 1 shows an illustration of an exemplary blood recovery apparatus 10, comprising a receptacle 12 supporting a strainer basket 14 for receiving a fluid retaining structure, such as a surgical sponge, generally designated by reference numeral 16. The apparatus 10 also comprises a flexible membrane or diaphragm 18 which covers the strainer basket 14 as a lid, to sealingly and removably secure the strainer basket 14 to the receptacle 12. The receptacle 12 also includes a port 20 coupled to a source of negative pressure i.e. pressure that is below surrounding (ambient) pressure, for facilitating the recovery of the fluid from the fluid retaining structure 16. Typically, a fluid 21, such as blood, is retained by the surgical sponge 16 which is constructed from an absorbent material, e.g., a low-count open-mesh gauze or washed gauze fabric sheet, such as woven cotton. The sheet may include a plurality of folds defining a multiple ply configuration of the sponge 16.

In more detail, the receptacle 12 is generally cylindrical in nature, comprising a base 22, sidewall 24 extending from the base 22 to define an interior chamber or cavity 25 having an opening 26 with a flange 27 extending outwardly therefrom. A reservoir 29 for the recovered fluid is formed in the chamber 25, and the port 20 is located in the sidewall 24, and adjacent to the opening 26. Generally, the strainer basket 14 is bowl-shaped and includes a perforated body 28 with a plurality of apertures 30 therethrough, and a flange 32 extending from the strainer basket opening 34. The apertures 30 extend through body 28 to allow for fluid, such as recovered blood 21, to pass therethrough. The receptacle flange 27 and the strainer basket flange 32 sealingly but removably engage each other, such that the strainer basket 14 fits snugly on the receptacle 12. The diaphragm 18 is dimensioned to cover the strainer basket opening 34, and comprises a generally uniform thickness across its entire diametric dimension, and a peripheral snap ring 36 defining the outer periphery. The peripheral snap ring 36 is shaped to matingly engage the flanges 27 and 32, thus sealingly and removably securing the strainer basket 14 to the receptacle 12. Preferably, the diaphragm 18 is semi-rigid, or is fabricated from a material having a density that allows the diaphragm 18 to be moved in response to the negative pressure within the interior chamber 25. Suitable materials for the diaphragm 18 may include plastic, such as, thermoplastic urethane (TPU) or thermoplastic elastomer (TPE), among others. The diaphragm 18 may also include a durable, rigid cover to shield the diaphragm 18 from damage due to sharp surgical instruments or other objects.

The port 20 extends from the interior chamber 25 of the receptacle 12 through the sidewall 24, with a spout 38 extending from the other side of the sidewall 24. Accordingly, a passageway 40 is formed to provide fluid communication with the chamber 25. The spout 38 may comprise a connector for coupling a hose to the source of negative pressure which provides a suction force, such as a suction device or vacuum terminal 42, such as that found in a hospital or laboratory environment. The connector may include a valve mechanism for permitting only air flow from the chamber 25, while impeding the flow of blood therethrough.

Figure 2:
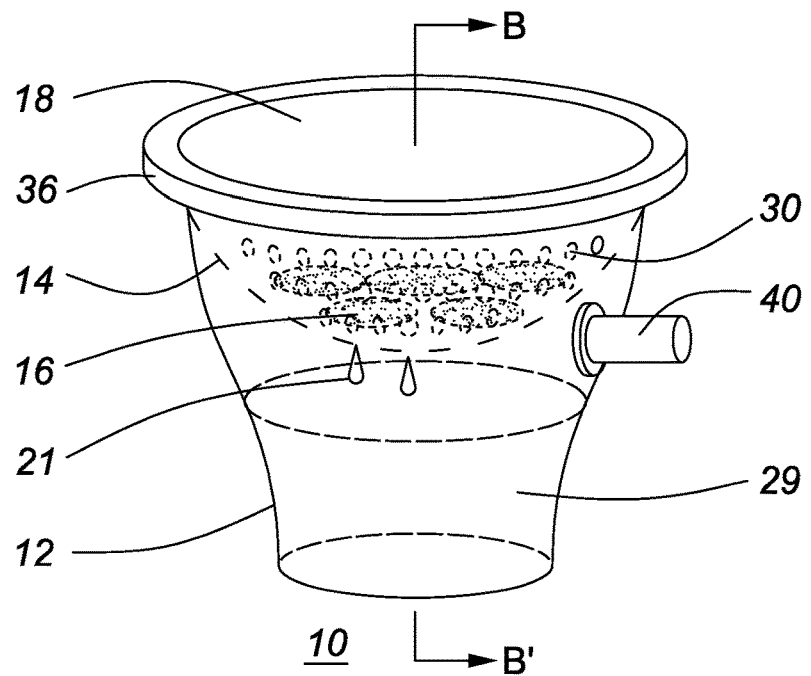
FIG. 2 shows the apparatus of FIG. 1 in its assembled form.
Figure 3:
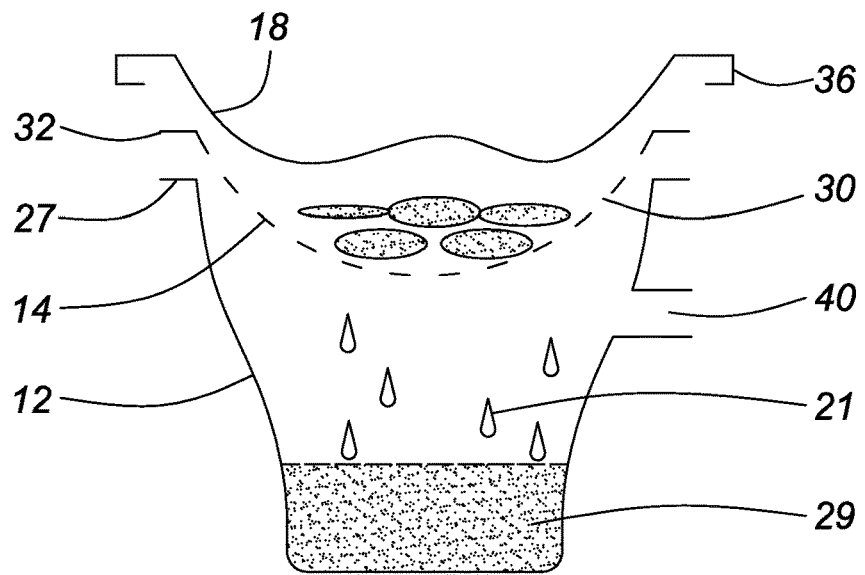
FIG. 3 shows a cross-section of the apparatus of FIG. 2 along line B-B'.

In operation, the apparatus 10 is easily assembled by placing the strainer basket 14 on the receptacle 12 such that the strainer basket flange 32 is supported by the receptacle flange 27, as shown in FIGS. 2 and 3. Blood-laden surgical sponges 16 are removed from a surgical site or a site with blood loss, and introduced into the strainer basket 14 via the opening 34, and come to rest on the perforated body 28. Typically, a predetermined number of blood-laden surgical sponges 16 are placed in the strainer basket 14 such that the capacity of the reservoir 29 is not exceeded, otherwise the efficiency of the vacuum terminal 42 may be compromised. The diaphragm 18 is placed over the strainer basket 14 and the snap ring 36 forces the flanges 27 and 32 together to create an air-tight seal. As such, air may only escape from the assembled apparatus 10 via the port 20. A suitable hose is connected to the connector to convey the pressure by the vacuum terminal 42.

Generally, as the vacuum terminal 42 draws air out of the chamber 25, and from the strainer basket 14 via the apertures 30, a partial vacuum is created within the assembled apparatus 10, and the negative pressure causes the diaphragm 18 to collapse on the blood-laden sponges 16, thus compressing the sponge 16, as shown in FIG. 2. The diaphragm 18, however, remains sealingly engaged to the receptacle 12 via the snap ring 36, thus maintaining the air-tight seal. Accordingly, the combined forces imparted by the diaphragm 18 and the negative pressure forces the blood out of the blood-laden sponges 16, which flows into the reservoir 29 via the apertures 30. Since the negative pressure is dispersed over the entire area of the perforated body 28, instead of being concentrated over a smaller area, the potential hemolytic effects due to the negative pressure are potentially minimized. Once a substantial amount of blood has been forced out of the sponges 16, or after a predetermined time, the vacuum terminal 42 may be stopped. For instance, the predetermined time may be correlated to the known time period required to recover the most blood for a predetermined number of sponges 16. The volume of the recovered blood 21 in the reservoir 29 may be measured via indicia on the receptacle 12, thus providing an effective means for monitoring the blood loss from the patient, without using prior art sponge-weighing methods.

After the vacuum terminal 42 has been stopped, the hose is disconnected and the diaphragm 18 is removed from the receptacle 12 by prying open the snap ring 36. The spent or compressed surgical sponges 16 are removed from the strainer basket 14 for re-use, or disposal. Typically, the number of surgical sponges 16 in use during a surgical procedure is known which allows for full accounting of the surgical sponges 16 prior to closing an incision, thus ensuring patient safety. The recovered blood 21 in the receptacle 12 may then be emptied to allow for recovered blood from a new batch of blood-laden surgical sponges 16. The receptacle 12 may be emptied by a variety of ways, such as, pouring the recovered blood 21 out into another container or suctioning the recovered blood 21 via the receptacle opening 26. Accordingly, the receptacle 12 may include a handle depending from the sidewall 24 to facilitate pouring, and transport of the receptacle 12, or apparatus 10.

Alternatively, the apparatus 10 may include a drainage assembly comprising an outlet in the sidewall 24 and adjacent to the base 22, with a one-way valve to control egress of the recovered blood 21 from the reservoir 29 through a tapered spout. Tubing may be connected to the spout to supply the recovered blood 21 to a blood processing device, such as a cell saver machine or cardiopulmonary bypass (CPB) machine. A typical cell saver machine collects, filters, washes and returns the patient's blood to the patient, such that a closed circulation loop with minimal storage can be maintained at all times. The cell saver may also measure the volume of the recovered blood 21. Alternatively, the recovered blood 21 may be dispensed into another vessel, such as a basin, via the spout, and the blood is then transferred therefrom to the cell saver machine or CPB machine.

Although both the cell-saver machine and the CPB machine typically include filtering mechanisms for the patient's blood prior to being reinfused into the patient, a filter may be included with the perforated body 28 to remove clots, debris, particulates or foreign material that may be soaked up by the sponges 16. Therefore, the filter is operable to permit blood to pass therethrough into the reservoir 29, while acting as a barrier to the clots, debris, particulates or foreign material. The side wall 24 of the receptacle 12 may include a Heparin coating, or any other suitable anticoagulant, to delay the clotting of the recovered blood 21, which may depend on the size of the blood reservoir 29, the duration the recovered blood 21 is stored in the reservoir 29, or the frequency of blood 21 removal from the reservoir 29.

Generally, the apparatus 10 may be fabricated from plastic materials and is for single-use only in order to enhance patient safety. Therefore, at the completion of the surgical procedure, all the components of the apparatus 10 are accounted for, and disposed of in a similar manner as the other bio-hazard materials.

Figure 4:
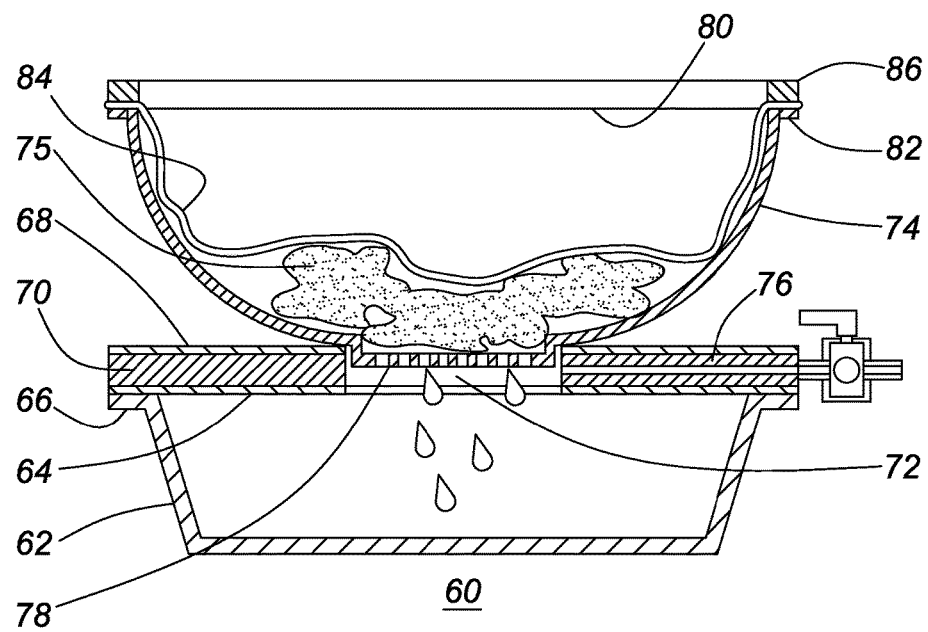
FIG. 4 shows another exemplary apparatus for recovering blood, in another embodiment.

In another exemplary embodiment, an exemplary blood recovery apparatus 60 comprises a receptacle 62 with an opening 64 having a flange 66 extending outwardly therefrom, as shown in FIG. 4. A lid 68 dimensioned to cover the opening 64 includes a peripheral edge 70 which rests on the flange 66. The lid 68 also comprises an aperture 72 disposed centrally to locate a bowl 74 which receives blood-laden sponges 75. The cross-sectional thickness of the lid 68 is dimensioned to permit a passageway to be formed from the aperture 72 to the peripheral edge 70. Located within the passageway is a tubing 76 with one end exposed to the opening 64, and extending beyond the peripheral edge 70, to provide fluid communication with the aperture 72. The other end of the tubing 76 is connected to a negative pressure source, such as a vacuum terminal. The tubing 76 may include valve means for controlling fluid flow therethrough, and a pressure regulator to measure and control the pressure within the apparatus 60. The bowl 74 comprises a body with a perforated base 78 dimensioned to fit snugly and sealingly within the aperture 72. The bowl 74 further comprises an opening 80 with a flange 82 extending therefrom. A flexible membrane 84 affixed to an annular snap ring 86 is placed over the opening 80, such that the snap ring 86 engages the flange 82 to secure to the flexible membrane 84 to the bowl 74. Accordingly, an air-tight chamber is defined by the flexible membrane-covered bowl 74 and the receptacle 62. Similar to the diaphragm 18, the flexible membrane 84 may also include a durable, rigid cover to shield the flexible membrane 84 from damage due to sharp surgical instruments or other objects.

In operation, the bowl 74 is placed within the aperture 72 and blood-laden sponges 75 are introduced into the bowl 74. Next, the flexible membrane 84 is secured to the bowl opening 80 and then the external force is applied. Accordingly, as air is drawn from the air-tight chamber the flexible membrane 84 is caused to collapse on the blood-laden sponges 75, compressing the blood-laden sponges 75. The negative pressure and the collapsed flexible membrane 84 on the blood-laden sponges 75 forces the sponges 75 against the perforated base 78 to urge the blood out. By maintaining the pressure within a predetermined range, negative pressure-induced hemolysis of the blood components may be substantially suppressed. Additionally, any potential hemolytic effects due to exposure to air are substantially minimized since the blood is not exposed to air during operation of the apparatus 60. Similar to the receptacle 12, the receptacle 62 may also include a handle to facilitate transport of the receptacle 62 or apparatus 60, or pouring the recovered blood into another vessel. The receptacle 62 may also comprise a drainage assembly comprising an outlet in the sidewall of receptacle 64, with a one-way valve for dispensing the blood or connecting to a cell saver machine or cardiopulmonary bypass (CPB) machine.

Figure 5:
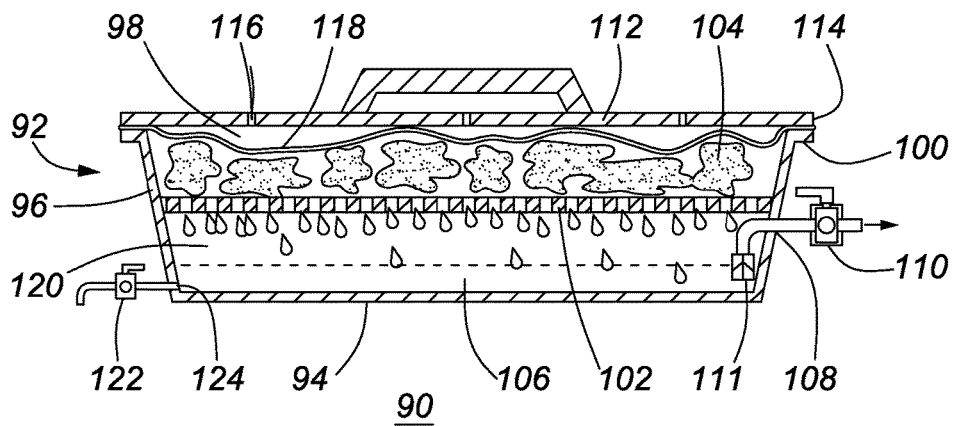
FIG. 5 shows another exemplary apparatus for recovering blood, in yet another embodiment.
Figure 6:
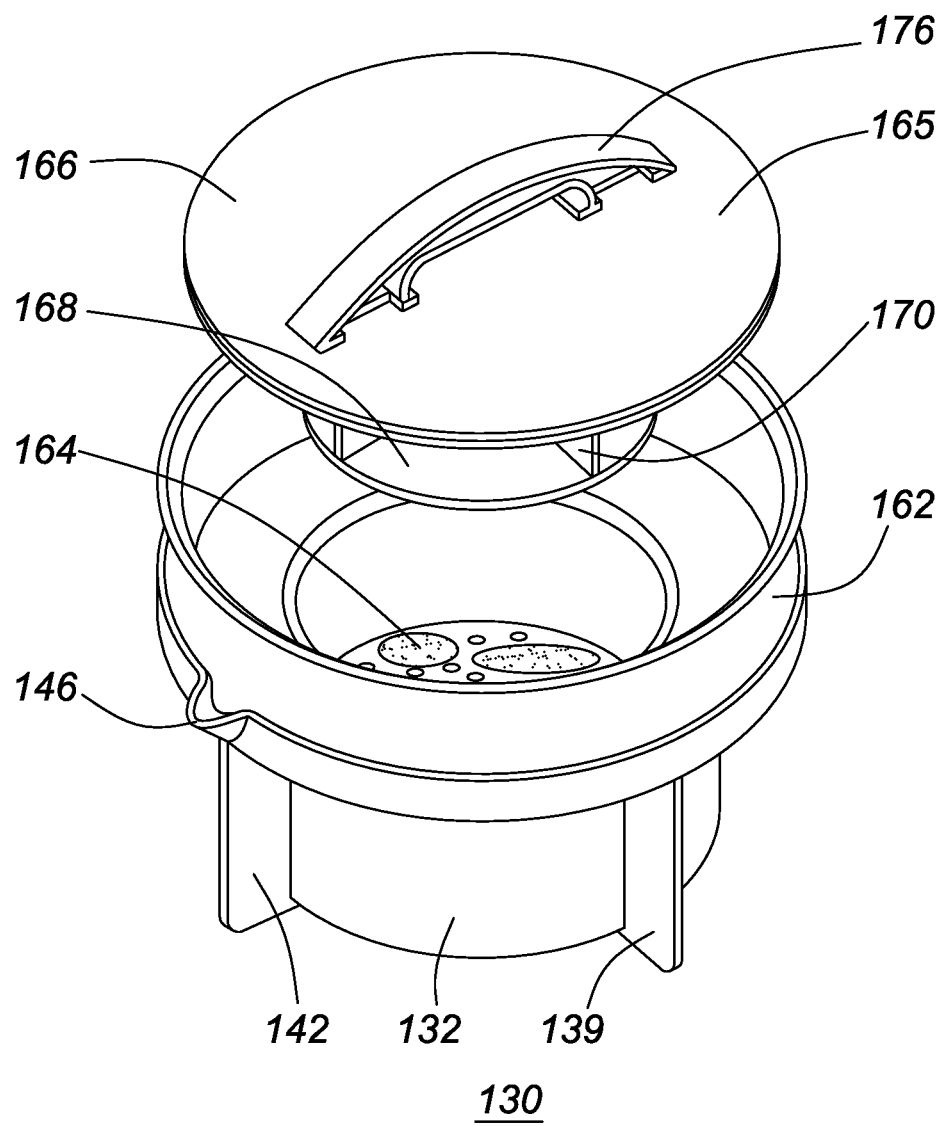
FIGS. 6 to 12 show different views of another exemplary apparatus for recovering blood, in yet another embodiment.
Figure 7:
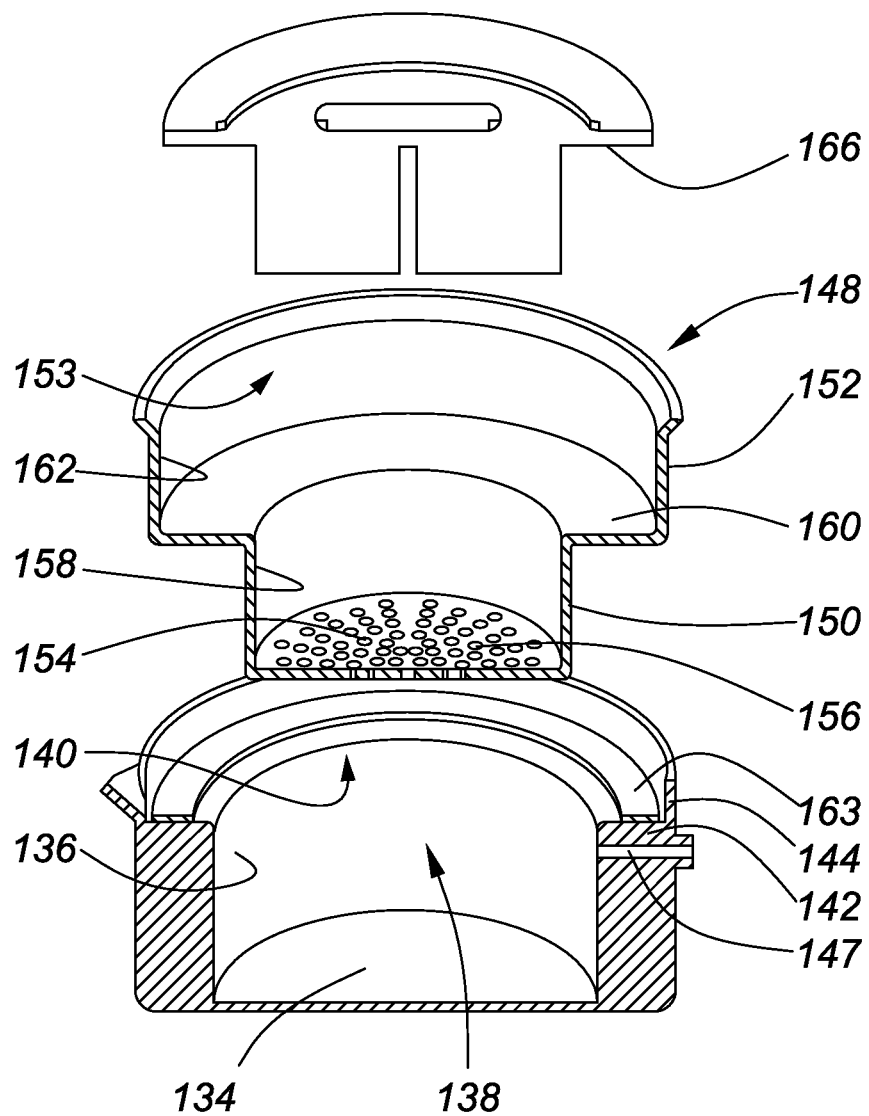

In yet another exemplary embodiment, an exemplary blood recovery apparatus 90 comprises a receptacle 92 with a base 94, a sidewall 96, and an opening 98 having a flange 100 extending outwardly therefrom, as shown in FIG. 5. Located between the base 94 and the opening 98 is a perforated platform 102 on which blood-laden sponges 104 rest, and a reservoir 106 for the recovered blood is formed below the perforated platform 102. The sidewall 96 includes one port 108 extending therethrough that connects via a line to a source of negative pressure, such as a vacuum terminal. The port 108 or the line is associated with a valve 110 for controlling fluid flow therethrough, or for preventing reverse flow, and the valve 110 may include a filter for permitting through passage of air only. In addition, a pressure regulator within the receptacle 92 may be included to measure and control the pressure, thus suppressing or minimizing possible hemolytic effects of the negative pressure. A float valve 111 within the reservoir 106 may be included to stop the vacuum terminal, once a float included therein, and rises with the level of the recovered blood within the reservoir 106, reaches a predetermined level. A lid 112 dimensioned to cover the opening 98 includes a peripheral edge 114 which rests on the flange 100. The lid 112 also includes at least one aperture 116 therethrough in communication with the exterior of the receptacle 92. Affixed to the peripheral edge 114 is a flexible membrane 118 in close contact with the blood-laden sponges 104. The lid 112 is secured to receptacle 92 by forcing the peripheral edge 114 of the lid 112 to the flange 100, such that an air-tight chamber 120 is defined between the flexible membrane 114 and the base 94.

In operation, as air is drawn from the air-tight chamber 120 the flexible membrane 118 is caused to collapse on the blood-laden sponges 104 and compress the blood-laden sponges 104. The atmospheric pressure, in combination with the negative pressure and the collapsing flexible membrane 118 forces the sponges 104 against the perforated platform 102 to urge the blood out of the sponges 104. The recovered blood is collected in the reservoir 106 and may be emptied via a drainage assembly 122 connected to another port 124 adjacent to the base 94. Alternatively, the drainage assembly 122 may be connected to a cell saver machine or cardiopulmonary bypass (CPB) machine. Similar to receptacle 12, the receptacle 92 may also include a handle to facilitate transport of the receptacle 92 or apparatus 90, or pouring the recovered blood into another vessel.

In yet another exemplary embodiment, a blood recovery apparatus 130 comprises a receptacle 132 with a base 134, a sidewall 136 defining an interior chamber 138, with an opening 140, as shown in FIGS. 6 to 12. The sidewall 136 also includes ribs 139 depending from the base 134 to the opening 140, and a seat 142 is formed around the perimeter of the opening 140 and extending away from the opening 140, and terminating perpendicularly with a ring wall 144. A spout 146 is formed within a portion of wall 144, and a port 147 is defined through the sidewall 136 and is connected via a line to a source of negative pressure, such as a vacuum terminal (not shown). A valve for controlling fluid flow therethrough, or for preventing reverse flow, is included, and may include a filter for allowing air only therethrough. The apparatus 130 also comprises a strainer basket 148 with a bottom portion 150 dimensioned to be accommodated within the interior chamber 138 and a top portion 152 with an opening 153, such that the top portion 152 rests on the seat 142. The strainer basket 148 further comprises a perforated base 154 with a plurality of apertures 156 extending therethrough, with a bottom portion sidewall 158 depending therefrom and terminating at the top portion 152. The apertures 156 are appropriately dimensioned to enhance drainage of the recovered blood into the receptacle 132, and may vary in size and/or shape. A flange 160 is formed with the bottom portion wall 158 and a top portion wall 162, such that the bottom portion wall 158 and the top portion wall 162 are separated by the flange 160 resting on the seat 142. Between the seat 142 and the flange 160 is a gasket or a seal member 163, such as an O ring, which provides an air-tight seal between the strainer basket 148 and the receptacle 132, during operation.

Figure 9:
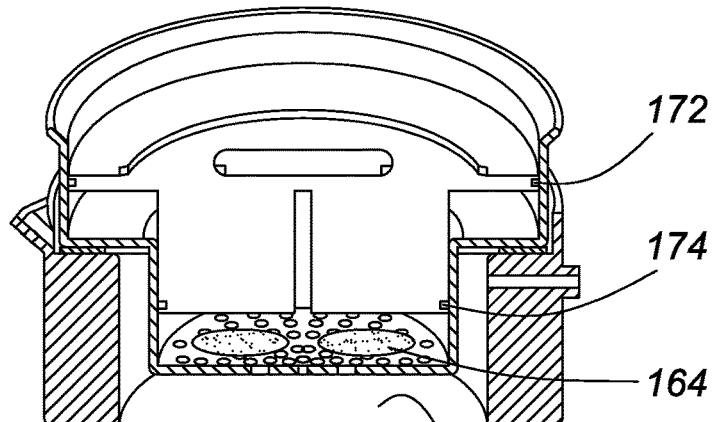
Figure 10:
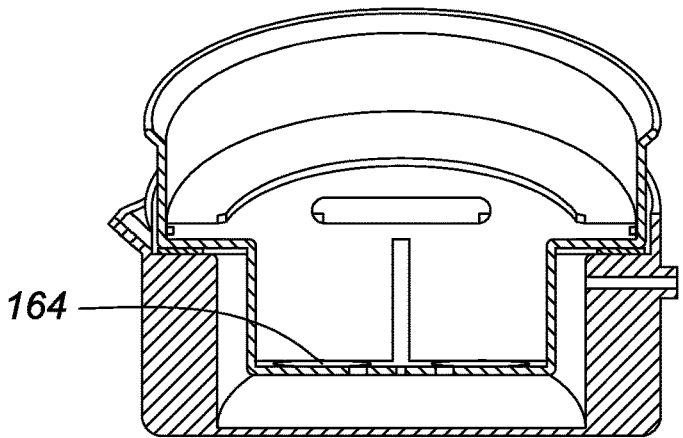
Figure 11:
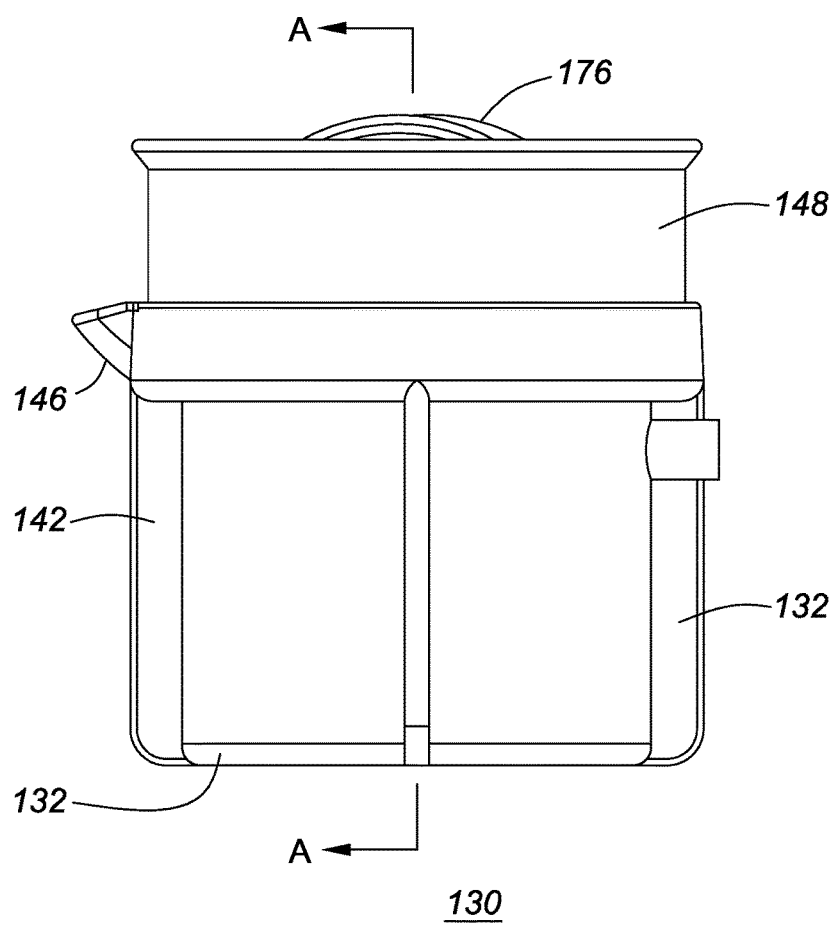
Figure 12:
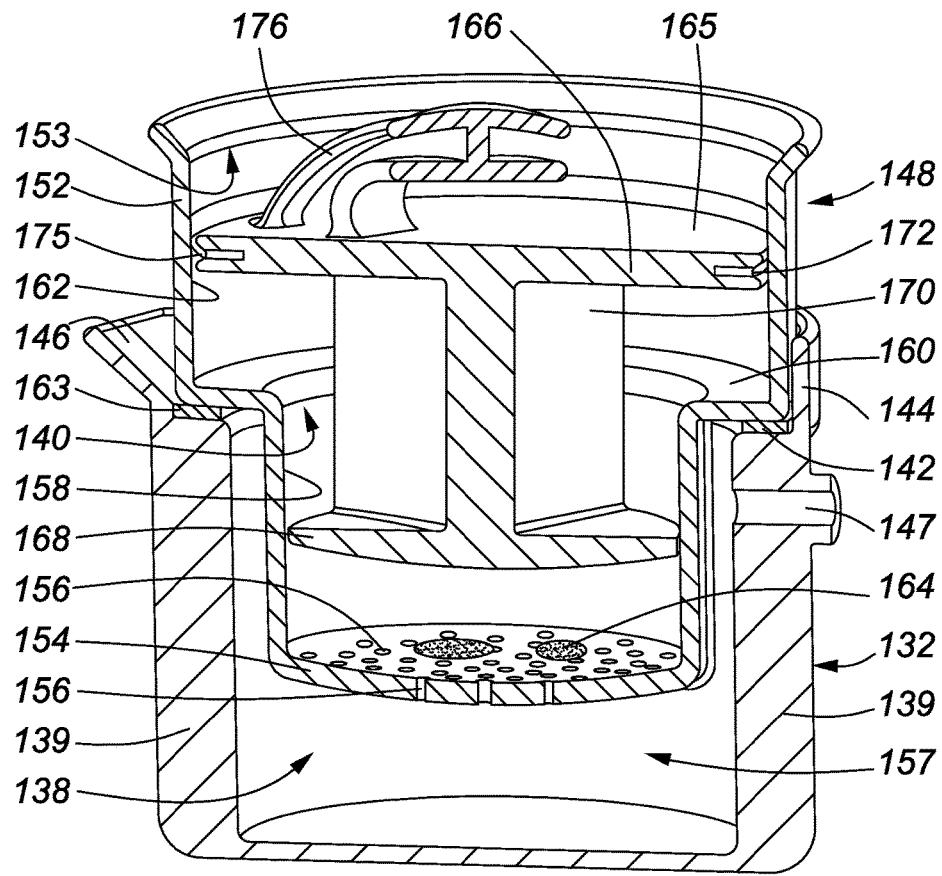

Blood-laden sponges 164 are received via the opening 153 and come to rest on the perforated base 154, and any recovered blood from the sponges 164 flows via the apertures 156 into a reservoir 157 formed in the interior chamber 138. A lid 165 is introduced via the opening 153 and exerts pressure on the blood-laden sponges 164 to force the blood out. The lid 165 comprises two disc-shaped piston heads 166 and 168 dimensioned to engage the top portion wall 162 and the bottom portion wall 158, respectively. The top disc-shaped piston 166 and the bottom disc-shaped piston 168 are separated by a plurality of ribs 170. The edge of the disc-shaped piston 166 includes a seal member 172, such as an O ring, or other suitable seal, which engages the wall 162 of the strainer basket 148. Accordingly, a portion of the seal member 172 is secured within a recessed channel 175 formed within the edge, while another portion of the seal member 172 extends outside the channel 175 to engage the wall 162. Therefore, when the lid 165 is introduced in the strainer basket 148, the seal member 172 sealingly engages the top portion wall 162, to form an air-tight chamber between the piston 166 and the base 134. During operation, as air is drawn out of the interior chamber 138 by the vacuum terminal, the negative pressure forces the disc-shaped pistons 166 and 168 towards the perforated base 154, thus magnifying the force exerted on the blood-laden sponges 164. The action of the two disc-shaped pistons 166 and 168 moving simultaneously towards the perforated base 154 results in a "double" high-pressure phenomenon on the sponges 164, which enhances blood recovery therefrom, as shown in FIGS. 9 and 10. For example, with the exemplary two disc-shaped pistons 166 and 168 dimensioned at 6.25 in. and 4.2 in., respectively, when the pressure source conveys a pressure of 400 mmHg (or 7.735 psi), then the disc-shaped piston 166 is subject to a force of approximately 237 lb (i.e. $7.735 (6.25/2)^2 \pi$), and this force translates to approximately 885 mmHg (i.e. $237/((4.2/2)^2 \pi)$)=17.3 psi) as the resultant pressure to the disc-shaped piston 168. Accordingly, the resultant pressure on the sponges 164 is intensified by this arrangement, with a gain ratio of approximately 2.2. Therefore, the magnitude of the negative pressure conveyed to the receptacle 132 may be lowered to minimize hemolysis, while relying more on the intensified pressure conveyed to the disc-shaped piston 166 to force the blood out of the sponges 164. Once the blood has been drawn out of the sponges 164 the suction force is stopped, and the lid 165 is removed from the strainer basket 148 by pulling on a handle means 176, and the spent sponges 164 are removed from the perforated base 154. Subsequently, the strainer basket 148 is removed from the receptacle 132 and the recovered blood is poured out via the spout 146. Advantageously, since the apparatus 130 comprises only three major parts, that is, the receptacle 132, the strainer basket 148 and the lid 165, the apparatus 130 is easily assembled or disassembled to facilitate emptying of the reservoir 157.

The recovered blood is collected in the reservoir 157 and may be emptied via the spout 146. Alternatively, a drainage assembly is connected to another port adjacent to the base 134 for emptying the reservoir 157. Further, the drainage assembly may be connected to a cell saver machine or cardiopulmonary bypass (CPB) machine.

In addition, a pressure regulator may be included to measure and control the pressure within the receptacle 132. While the handle means 176 aids in the placement of the lid 165 in the strainer basket 148, and removal of the lid 165 from the strainer basket 148, it may also be facilitate the application of a force for manual operation of the apparatus 130.

Similar to apparatus 10, the apparatus 130 may include a filter with a perforated body to remove clots, debris, particulates or foreign material that may be soaked up by the sponges 16.

In yet another embodiment, positive pressure is applied to force down the lid 165 of apparatus 130. As such, after the sponges 164 and the lid 165 have been introduced in the strainer basket 148, a cover is placed over the opening 153 to create an air-tight seal. Positive pressure is introduced via an inlet in the cover. The positive pressure may be applied by regulated compressed air or by an air pump. In this embodiment, the outlet 147 to the source of negative pressure is closed, and thus inoperable. Accordingly, the system may be adapted for use with a negative pressure source vacuum source and/or a positive pressure source. Alternatively, a pressure may be applied manually, for example, the handle 176 of lid 165 is grasped and a force is exerted to drive the pistons 166 and 168 towards the sponges 164 resting on the perforated base 154. Electro-mechanical means such as an electric motor coupled to means for translating rotational motion into longitudinal motion to the lid 165 may also be employed. As described above, the action of the two disc-shaped pistons 166 and 168 moving simultaneously towards the perforated base 154 results in a "double" high-pressure phenomenon on the sponges 164, which enhances blood recovery therefrom.

Figure 8:
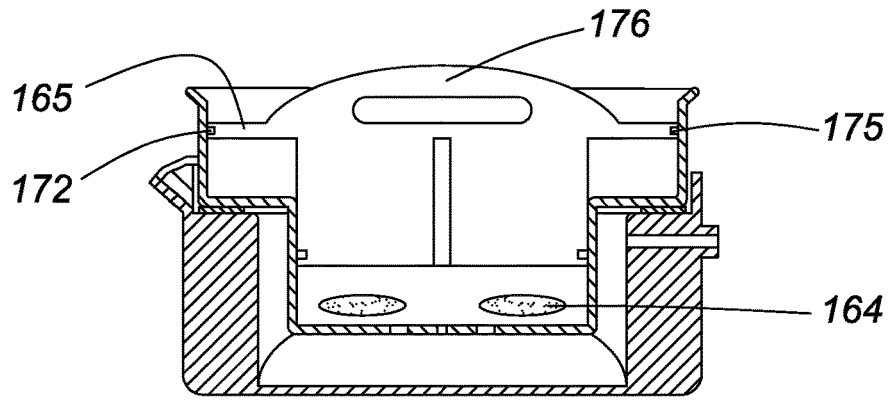

In yet another exemplary embodiment, an edge of the bottom disc-shaped piston 168 also includes a seal member, such as an O ring, or other suitable seal, secured within a recessed channel 175 formed within the edge, as shown FIGS. 8 to 10. This seal member engages the wall 162 of the strainer basket 148 and minimizes the migration of any recovered blood upward or away from the base 134.

In yet another exemplary embodiment, the blood recovery apparatus 10 comprises a cylindrical housing with a sidewall extending from a base to an opening. Located between the base and the opening is a perforated platform on which blood-laden sponges rest. A port defined in the sidewall is connected to source of negative pressure, and a reservoir for the recovered blood is defined between the base and the port. A disc-shaped piston is introduced into the housing, and sealingly engages the sidewall to create an air-tight volume between the piston and the base. As air is drawn out of the housing, the negative pressure causes the piston to descend and compress the sponges. Accordingly, the negative pressure and the force from the piston cause the blood to drawn from the sponges. The recovered blood may be poured out of the housing, or alternatively, the housing may include another port connected to a drainage assembly for emptying the reservoir. The drainage assembly may be connected to a cell saver machine or cardiopulmonary bypass (CPB) machine. Similar to the receptacle 12, the housing may also include a handle to facilitate transport of the housing, or pouring the recovered blood into another vessel.

In yet another exemplary embodiment, the blood recovery apparatus 10 comprises a flexible housing with a resealable orifice for introducing blood-laden sponges into the housing and a port connected to a housing via a hose. The housing is also connected to a source of negative pressure, such that a partial vacuum is created in the reservoir. In turn, the partial vacuum causes the housing to compress the sponges, and causes the blood to be drawn from the sponges, and flow into the reservoir. The housing interior may comprise a mesh abutting the sponges, which promotes the flow of blood out of the housing by maintaining fluid channels. Alternatively, the housing interior comprises ribs formed to prevent fluid channels from collapsing as the pressure drops. The port and/or the hose to the reservoir may include a valve for regulation of fluid flow, or a pressure intensifier, and a filter allowing passage of air only. Spent sponges may be removed from the housing via the orifice, and a fresh batch of blood-laden sponges may be introduced into the housing. Hemolytic effects due to pressure and air may be substantially minimized using previously discussed techniques.

Although in the foregoing embodiments the method and system for recovering blood have been described as being useful in an intra-operative setting, the method and system are also operable or potentially viable in a post-operative care setting, such as a recovery unit or care unit, including other applications.

In any of the above embodiments, in order to delay the clotting of the recovered blood, a Heparin coating, or any other suitable anticoagulant, may be added to the interior walls of the reservoir in contact with blood.

In another embodiment, any of the exemplary apparatus described above may be used in other commercial applications, such as forcing fluid or liquid from any absorbent material. For example, in one application oil is forced out of oil-soaked sponges or rags in environmental clean-up procedures. Another application may be in the janitorial cleaning services or household cleaning, for wringing liquid-absorbent materials or devices, such as mops, sponges or rags. As those of skill will appreciate, the afore-mentioned apparatuses may be modified to suit the desired application.

Benefits, other advantages, and solutions to problems have been described above with regard to specific embodiments. However, the benefits, advantages, solutions to problems, and any element(s) that may cause any benefit, advantage, or solution to occur or become more pronounced are not to be construed as critical, required, or essential features or elements of any or all the claims. As used herein, the terms "comprises," "comprising," or any other variations thereof, are intended to cover a non-exclusive inclusion, such that a process, method, article, or apparatus that comprises a list of elements does not include only those elements but may include other elements not expressly listed or inherent to such process, method, article, or apparatus. Further, no element described herein is required for the practice of the invention unless expressly described as "essential" or "critical."

The preceding detailed description of exemplary embodiments of the invention makes reference to the accompanying drawings, which show the exemplary embodiment by way of illustration. While these exemplary embodiments are described in sufficient detail to enable those skilled in the art to practice the invention, it should be understood that other embodiments may be realized and that logical and mechanical changes may be made without departing from the spirit and scope of the invention. For example, the steps recited in any of the method or process claims may be executed in any order and are not limited to the order presented. Further, the present invention may be practiced using one or more servers, as necessary. Thus, the preceding detailed description is presented for purposes of illustration only and not of limitation, and the scope of the invention is defined by the preceding description, and with respect to the attached claims.

The invention claimed is:

1. A method for recovering blood for autologous with a blood absorbent structure for blood transfusion into a patient, the method comprising the steps of:
    absorbing blood from a surgical site associated with said patient with said blood absorbent structure;
    introducing said blood absorbent structure into a perforated strainer received by a vessel;
    conveying pressure to said vessel to apply a force on a member movable within said perforated strainer to contact said blood absorbent structure and cause egress of said blood from blood absorbent structure to flow through said perforated strainer for collection;
    wherein said strainer comprises a small diameter lower section joined to a large diameter upper section, said small diameter lower section having a base with a plurality of apertures, and said blood absorbent structure rests on said base; and
    wherein said member is a piston comprising an upper piston head for engaging said large diameter upper section and a lower piston head for engaging said small diameter lower section.

2. The method of claim 1, wherein said pressure is provided by at least one source of negative pressure and positive pressure.

3. The method of claim 2, wherein said force is provided by at least one of manually, pneumatically, mechanically, electro-mechanically and electrically.

4. The method of claim 3, wherein said pressure on said upper piston head is multiplied by said lower piston head to provide intensified pressure on said blood absorbent structure, such that the arrangement of said lower piston head and said upper piston provides a mechanical advantage for efficient blood recovery from said blood absorbent structure.

5. The method of claim 4, wherein said pressure conveyed to said large diameter section is multiplied by a factor of at least two to said small diameter lower section.

6. The method of claim 4, wherein said blood absorbent structure is one of a surgical sponge, gauze, towel and swab.

7. The method of claim 1, wherein said pressure minimizes hemolytic effects on blood components of said absorbed blood.

8. The method of claim 1, wherein said pressure is maintained at a predetermined level to minimize hemolytic effects on blood components of said absorbed blood.

9. The method of claim 1, wherein said blood absorbent structure is one of a surgical sponge, gauze, towel and swab.

10. A method for recovering blood for autologous blood transfusion into a patient, the method comprising the steps of:
    absorbing blood from a surgical site associated with said patient with a surgical sponge;
    introducing said surgical sponge into a perforated strainer received by a vessel;
    conveying pressure to said vessel to apply a force on a piston to act on said surgical sponge and cause egress of said blood from said surgical sponge to flow through said perforated strainer into a reservoir;
    wherein said perforated strainer comprises a small diameter lower section joined to a large diameter upper section, said small diameter lower section having a base with a plurality of apertures; and
    wherein said piston comprises an upper piston head for engaging said large diameter upper section and a lower piston head for engaging said small diameter lower section.

11. The method of claim 10, wherein said pressure is provided by at least one source of negative pressure and positive pressure.

12. The method of claim 11, wherein said force is provided by at least one of manually, pneumatically, mechanically, electro-mechanically and electrically.

13. The method of claim 10, wherein said pressure on said upper piston head is multiplied by said lower piston head to provide intensified pressure on said surgical sponge, such that the arrangement of said lower piston head and said upper piston provides a mechanical advantage for efficient blood recovery from said surgical sponge.

14. The method of claim 13, wherein said pressure conveyed to said large diameter section is multiplied by a factor of at least two to said small diameter lower section.

15. The method of claim 14, wherein said upper piston head engages an inner wall of said large diameter section and said lower piston head engages an inner wall of said small diameter section such that an air-tight cavity is defined between said upper piston head and a base of said vessel.

16. The method of claim 10, wherein said pressure minimizes hemolytic effects on blood components of said absorbed blood.

17. The method of claim 10, wherein said pressure is maintained at a predetermined level to minimize hemolytic effects on blood components of said absorbed blood.

18. A device for recovering blood for autologous blood transfusion into a patient, the device having:
    a vessel for receiving a surgical sponge for absorbing blood from a surgical site associated with said patient;
    a perforated strainer received by said vessel,
    a piston;
    a source of pressure coupled to said vessel; and
    whereby said piston is caused to travel within said strainer by a force provided by negative pressure; and
    whereby said piston acts on said surgical sponge to cause egress of said blood from said surgical sponge to flow through said perforated strainer into a reservoir associated with said vessel;
    wherein said strainer comprises a body having a small diameter lower section joined to a large diameter upper section, said small diameter lower section having a base with a plurality of apertures, wherein said surgical sponge rests on said base; and
    wherein said piston comprises an upper piston head for engaging said large diameter upper section and a lower piston head for engaging said small diameter lower section.

19. The device of claim 18, wherein said pressure on said upper piston head is multiplied by said lower piston head to provide intensified pressure on said surgical sponge, such that the arrangement of said lower piston head and said upper piston provides a mechanical advantage for efficient blood recovery from said surgical sponge.

* * * * *